United States Patent
Lenz et al.

(10) Patent No.: US 7,226,475 B2
(45) Date of Patent: Jun. 5, 2007

(54) STENT WITH VARIABLE PROPERTIES

(75) Inventors: Jason T. Lenz, Maplewood, MN (US); Jonathan Swift Stinson, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 472 days.

(21) Appl. No.: 10/150,117

(22) Filed: May 18, 2002

(65) Prior Publication Data

US 2002/0138133 A1 Sep. 26, 2002

Related U.S. Application Data

(63) Continuation-in-part of application No. 09/437,049, filed on Nov. 9, 1999, now Pat. No. 6,428,569.

(51) Int. Cl.
*A61F 2/06* (2006.01)

(52) U.S. Cl. .................................................. 623/1.16

(58) Field of Classification Search ............... 623/1.16, 623/1.13, 1.15; 606/191, 195, 198, 194
See application file for complete search history.

(56) References Cited

U.S. PATENT DOCUMENTS

| | | | |
|---|---|---|---|
| 4,580,568 A | 4/1986 | Gianturco | 128/345 |
| 5,064,435 A | 11/1991 | Porter | 623/12 |
| 5,383,892 A * | 1/1995 | Cardon et al. | 606/198 |
| 5,443,511 A | 8/1995 | Ogawa et al. | 623/16 |
| 5,618,299 A | 4/1997 | Khosravi et al. | 606/198 |
| 5,645,559 A | 7/1997 | Hachtman et al. | 606/198 |
| 5,667,523 A | 9/1997 | Bynon et al. | 606/198 |
| 5,669,924 A | 9/1997 | Shaknovich | 606/108 |
| 5,683,450 A | 11/1997 | Goicoechea et al. | 623/1 |
| 5,693,085 A | 12/1997 | Buirge et al. | 623/1 |
| 5,733,303 A | 3/1998 | Israel et al. | 623/1.15 |
| 5,746,765 A | 5/1998 | Kleshinski et al. | 606/198 |
| 5,755,773 A | 5/1998 | Evans et al. | 623/1 |
| 5,800,525 A * | 9/1998 | Bachinski et al. | 606/200 |
| 5,807,404 A | 9/1998 | Richter | 623/1.16 |
| 5,824,052 A | 10/1998 | Khosravi et al. | 623/1.1 |
| 5,843,168 A | 12/1998 | Dang | 623/1 |
| 5,879,381 A | 3/1999 | Moriuchi et al. | 623/1.16 |
| 5,906,640 A | 5/1999 | Penn et al. | 623/1 |
| 5,916,264 A | 6/1999 | Von Oepen et al. | 623/1.15 |
| 5,938,697 A | 8/1999 | Killion et al. | 623/1 |
| 5,980,565 A | 11/1999 | Jayaraman | 623/1 |

(Continued)

FOREIGN PATENT DOCUMENTS

EP 0 878 173 B1 11/1997

(Continued)

OTHER PUBLICATIONS

Jostent® Coronary Stent Graft Product Information Brochure from Jomed® .

(Continued)

*Primary Examiner*—Kevin T. Truong
(74) *Attorney, Agent, or Firm*—Vidas, Arrett & Steinkraus, P.A.

(57) ABSTRACT

A stent having variable thickness with improved radiopacity, MRI compatibility, radial stiffness, and flexibility and to the method of making such stents.

19 Claims, 8 Drawing Sheets

U.S. PATENT DOCUMENTS

| | | | |
|---|---|---|---|
| 6,007,573 A | 12/1999 | Wallace et al. | 623/1 |
| 6,015,433 A | 1/2000 | Roth | 623/1 |
| 6,066,167 A | 5/2000 | Lau et al. | 623/1 |
| 6,099,559 A | 8/2000 | Nolting | 623/1 |
| 6,120,535 A | 9/2000 | McDonald et al. | 623/139 |
| 6,131,266 A | 10/2000 | Saunders | 29/557 |
| 6,159,238 A | 12/2000 | Killion et al. | 623/1.11 |
| 6,165,209 A | 12/2000 | Patterson et al. | 623/1.1 |
| 6,245,100 B1 | 6/2001 | Davila et al. | 623/1.13 |
| 6,261,320 B1 | 7/2001 | Tam et al. | 623/1.15 |
| 6,264,682 B1 | 7/2001 | Wilson et al. | 623/1 |
| 6,325,823 B1 * | 12/2001 | Horzewski et al. | 623/1.16 |
| 6,325,825 B1 | 12/2001 | Kula et al. | 623/1.3 |
| 6,331,191 B1 | 12/2001 | Chobotov | 623/1.44 |
| 6,676,701 B2 | 1/2004 | Rourke et al. | 623/1.39 |
| 6,852,123 B2 | 2/2005 | Brown | 623/1.15 |
| 2001/0044649 A1 | 11/2001 | Vallana et al. | 623/1.15 |
| 2001/0044650 A1 | 11/2001 | Simso et al. | 623/1.16 |
| 2004/0111142 A1 | 6/2004 | Rourke et al. | 623/1.1 |
| 2005/0107863 A1 | 5/2005 | Brown | 623/1.15 |

FOREIGN PATENT DOCUMENTS

| | | |
|---|---|---|
| WO | 95/31945 | 11/1995 |
| WO | 98/22045 | 5/1998 |
| WO | 99/22045 | 5/1998 |
| WO | 98/32412 | 7/1998 |
| WO | 98/49964 | 11/1998 |
| WO | 98/53765 | 12/1998 |
| WO | 99/30638 | 6/1999 |
| WO | 00/28922 | 5/2000 |
| WO | 01/00112 A1 | 1/2001 |
| WO | 01/08600 A2 | 2/2001 |
| WO | 01/34064 A2 | 5/2001 |

OTHER PUBLICATIONS

Histeopathological Evaluation of a Self-Expanding Arterial Liner (SEAL) in the Peripheral Vascular System of Dogs, Brennecke et al. Dialog Patent Search Dated Feb. 17, 1999.

U.S. Appl. No. 09/437,049, filed Nov. 09, 1999, Brown.

* cited by examiner

STENT WITH VARIABLE PROPERTIES

CROSS REFERENCE TO RELATED APPLICATIONS

This is a continuation-in-part of U.S. patent application Ser. No. 09/437,049 filed Nov. 9, 1999 now U.S. Pat. No. 6,428,569 the entire contents of which are incorporated by reference herein.

FIELD OF THE INVENTION

The present invention relates to intraluminal medical devices, in particular to endoprosthetic devices commonly referred to as stents. More particularly, the present invention relates to stents having improved properties such as improved radiopacity, MRI safety and compatibility, radial stiffness and flexibility, and to the method of making such stents.

BACKGROUND OF THE INVENTION

Stents and stent delivery devices are employed in a number of medical procedures and as such their structure and function are well known. Stents are typically cylindrical, radially expandable prostheses introduced via a catheter assembly into a lumen of a body vessel in a configuration having a generally reduced diameter, i.e. in a crimped or unexpanded state, and are then expanded to the diameter of the vessel. In their expanded state, stents support or reinforce sections of vessel walls, for example a blood vessel, which have collapsed, are partially occluded, blocked, weakened, or dilated, and maintain them in an open unobstructed state. They have also been implanted in the urinary tract and in bile ducts. Stents are advantageous because they can reduce the likelihood of restenosis, and because the patency of the blood vessel is maintained immediately after the intravascular treatment.

Stents are available in self-expanding and in inflation expandable versions which employ a dilatation balloon for expansion. Both versions are well known and widely available in a variety of designs and configurations, and are made from a variety of materials including plastics and metals with metals being more typically used.

For stent delivery, the stent and optionally a balloon, are positioned at the distal end of the catheter, around a core lumen. The stent and balloon are held down and covered by a sheath or sleeve. When the distal portion is in its desired location of the targeted vessel the sheath or sleeve is retracted to expose the stent. Self-expanding stents are typically in unexpanded state using a variety of methods including sheaths or sleeves, for example, during delivery to the site of deployment.

The catheter delivery system is advanced through the patients vascular system until the stent is at the desired location within a blood vessel, and then the expandable member is inflated on the catheter to expand the stent within the blood vessel. For the self-expanding variety, the sheath or sleeves may be retracted, leaving the stent free to self-expand. For the inflation variety, the expandable member, i.e. the balloon, may be expanded using a variety of methods such as through an inflation fluid, once the sheath or sleeves are removed, and the stent expands with the expandable member. The expandable member is then deflated and the catheter withdrawn, leaving the expanded stent within the blood vessel to hold the occluded or blocked vessel open.

In any case, the advancement of the stent through a patient's vasculature can involve traversing sharp bends and other obstacles which may require the stent to be highly flexible. Stent flexibility also permits the stent to be deployed in and conform to a tortuous section of a patient's vasculature.

It has also become highly desirable and common to employ a visualization technique referred to as radiographic fluoroscopy and magnetic resonance imaging (MRI), to allow the physician to accurately position and patency the stent at the desired location, and also to check the position during follow-up visits. The techniques require the stent to have good radiographic properties for fluoroscopy and good magnetic properties that avoid stent movement, floating, and image artifact during MRI.

One property is sometimes achieved at the expense of the other. Flexibility can be improved by decreasing the thickness of the material. On the other hand, radiopacity, for stents formed from stainless steel or NITINOL®, for example, is determined by the radiographic density of the material and the thickness of the stent tubing wall. Therefore, the use of thin material can reduce the radiopacity of the stent, making it more difficult to accurately visualize the stent. Conversely, the use of thicker material which can improve radiopacity, can reduce stent flexibility which can negatively impact the deliverability of the stent in a patient's vasculature.

MRI safety and compatibility is optimal when materials having low magnetic susceptibility are employed such as tantalum, titanium, niobium, and so forth. However, such materials are not necessarily optimum for properties such as flexibility, radial strength, and/or radiopacity, for example.

One method for improving the radiopacity is to deposit a thin surface coating or plating or a more radiographically dense material such as gold. This may change the properties of the stent, however, and these highly radiographic materials are often very costly.

Other desirable properties include radial strength so that the stent is resistant to elastic recoil and radial compression. This can also be difficult to achieve with a thin walled and small diameter stent.

SUMMARY OF THE INVENTION

In some embodiments of the present invention, the stent is of a closed cylindrical construction in which expansion is accompanied by deformation of the strut structure making up the body of the stent. Deformation, as used herein, is meant to include other deformation in addition to permanent deformation as used in the metallurgical sense. In accordance with this invention a suitable micro structure design can be obtained by dimensionally constructing a stent having a reduction ratio as compared to current coronary stents of 4:1 to 10:1. Note with reference to ratio reduction-current dimensions are thereby reduced by a factor of about 4-10.

Some micro structure stents in accordance with the present invention will preferably have about the following dimensions:

strut width 0.00025-0.002 inches
    strut thickness 0.00025-0.004 inches
    maximum PIN opening 0.002-0.020 inches diameter (current stent designs typically have a maximum PIN opening of around 0.025 inches to 0.050 inches in diameter).

The term "maximum PIN opening" as used herein describes micro openings in which the dimensions specify the largest which can be passed through the cell opening.

This applies as noted above to the expanded stent configuration. Typically, as a stent is expanded to larger diameters, the opening becomes larger. It is believed that using a maximum PIN opening specification that the concept of the present invention may be more readily applicable to stents of either open or closed cell geometries.

In some embodiments, the stents having a micro structure according to the present invention will also have a wall thickness of up to about 0.004 inches, which is not requirement of the invention, but provides adequate radiopacity and handling characteristics of the stent structure according to this embodiment.

In some embodiments, the present invention may include a stent within a stent wherein both stents, even though having larger openings than would be characterized as providing micro structure, may in fact provide micro structure by control of the registration of the openings in the stents as is more fully described below.

The present invention also relates to a stent having variable thickness of relatively thinner and thicker areas which exhibits improved flexibility, radiopacity, MRI safety and compatibility, and radial strength, and to a method of making the same.

The relatively thinner sections of the stent promote flexibility while the relatively thicker sections promote radiopacity and radial strength. Furthermore, materials may be selected so as to produce optimum MRI safety and compatibility as well, without sacrificing other properties.

In some embodiments, the stent is formed of a first tubular member and a second tubular member. The first tubular member has cut-out regions and the second tubular member is made of a thin walled construction. The tubular members may be advantageously formed from the same material, or they may be formed from different materials.

In one embodiment, the first tubular member is slightly larger in diameter than the second tubular member and is assembled over the second tubular member. Alternatively, the second tubular member may be slightly larger in diameter than the first tubular member and is assembled over the first tubular member.

The tubular members may be secured together using any method known in the art including, for example, welding, brazing, bonding, drawing, rolling, and so forth.

However, no mechanical securement other than mechanical contact is required. For example, an interference or line-to-line fit may be employed to secure the tubular members together. This technique may find particularly utility, for example, when the expansion of the medical device is conducted through mechanical means such as with an inflation member, for example, a dilatation balloon. Upon expansion with the dilatation balloon, the tubular members will be suitably pressed together thus remaining securely together in the implanted, i.e. expanded, configuration.

In another embodiment, sections of tubular members may secured together prior to forming the stent pattern. These sections may be secured together end to end, i.e. through a butt joint.

The tubular members may be advantageously formed of different materials, some of which have increased flexibility, such as shape memory alloys such as NITINOL®, for example, while others of which exhibit excellent fluoroscopic properties or MRI properties, i.e. those materials with high radiopacity such as gold, platinum, tantalum, and so forth, or those which have low magnetic susceptibility such as titanium and niobium, for example. The less fluoroscopic sections may be MRI compatible materials such as NITINOL®, or they may be strong materials such as stainless steel including 316L stainless steel, for example. In some embodiments, the sections formed of radiopaque materials are not as long as those formed of contrasting materials such as NITINOL® or stainless steel, for example. To increase radiographic contrast, the thickness of the radiopaque sections may be increased.

Alternatively, the sections may be formed from the same material but may be manufactured of varying thicknesses to obtain improved radiographic contrast and strength with thicker sections and improved flexibility with the thinner sections. These properties may be designed into the stent based on expansion properties as well.

In another embodiment, the stent is provided with increased flexibility, radial strength and radiographic contrast by providing the tubular member with a particular stent pattern. In particular, the pattern is an oval, a protuberance, or a honeycomb pattern.

In another embodiment, the stent has a substantially polygonal cross-section. In this particular embodiment, the inside surface of the polygonal preform may be machined, ground, etched and so forth thus producing sections of varying thickness. The stent pattern may then be cut from sections of the tube having the desired thicknesses in order to obtain optimum properties.

The embodiments described herein will lead to other embodiments of the invention, some of which are described in detail below. As with any stent design, many different designs are possible with respect to features such as flexibility, radiopacity, MRI compatibility, strength, etc. Thus, the geometries and configurations described below are included for illustrative purposes.

Other features and advantages of the invention will become apparent from the following detailed description, taken in conjunction with the accompanying drawings which illustrate, by way of example, the features of the invention.

BRIEF DESCRIPTION OF THE DRAWINGS

FIG. 11d is a cross-sectional view of the same tubular structure shown in FIG. 11a.

FIG. 12b is a cross-sectional view of the stent shown in FIG. 12a.

FIG. 13b is a cross-sectional view of the stent shown in FIG. 13a.

FIG. 14d shows an end view of the same stent pattern as shown in FIG. 14a.

DETAILED DESCRIPTIONS OF THE PREFERRED EMBODIMENTS

While this invention may be embodied in many different forms, there are described in detail herein specific preferred embodiments of the invention. This description is an exemplification only of the principles of the invention, and is not intended to limit the scope of the invention to the particular embodiments illustrated and described herein.

In some embodiments, the present invention includes a micro porous stent having a deformable structure. Generally, this is meant that the deformable struts of both self-expanding and mechanically-expandable stents already known in the art should be provided with micro porous structure. The fabrication of such stents is typically from flat sheet which is rolled then welded into a cylinder or from tubular stock.

Figure 1:
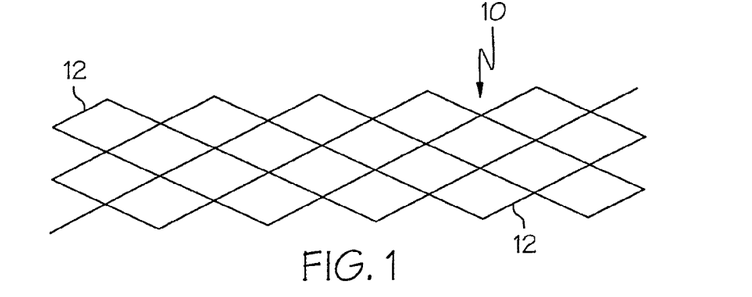
FIG. 1 is a schematic fragment showing a micro structure stent of the invention.

A first way to achieve micro structure in a stent involves simply making the struts and the openings of the stent extremely small. Such a stent would be comprised of a plurality of interconnected deformable struts arranged with respect to each other to provide a micro structure which facilitates support with a minimal disruption in the vessel of a body, the micro structure being characterized, after expansion, by about the following dimensions or smaller.

strut width 0.00025-0.002 inches
strut thickness 0.00025-0.004 inches
maximum PIN opening 0.002-0.20 inches Having reference to FIG. 1, there is shown in fragment a portion of a stent 10 of closed cell geometry in schematic form. This stent could be taken to be formed of wire or wires 12 into a cylindrical configuration to form the stent 10. On the other hand, the struts formed by wire 12 could also be manufactured by laser cutting struts 12 from tubular stock of an appropriate diameter.

Figure 2:
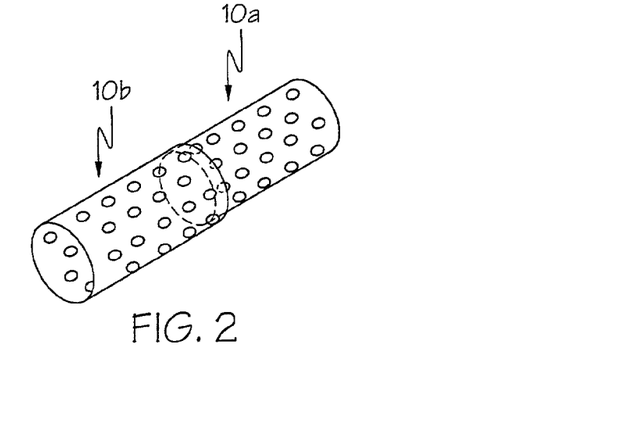
FIGS. 2 and 3 are schematic showings of a stent within a stent according to this invention.
Figures 3, 4:
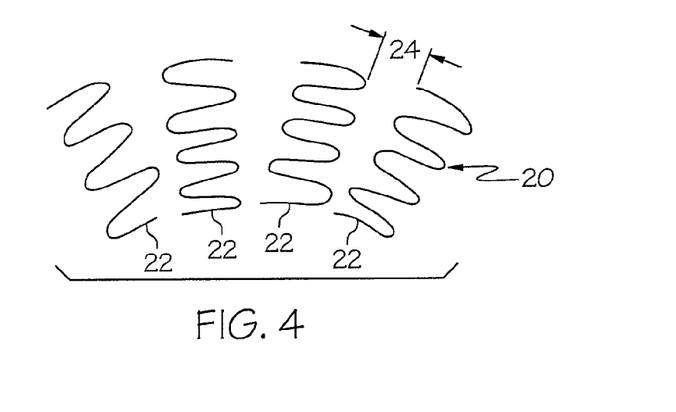
FIG. 4 is a schematic showing of a section of a stent made up of serpentine annular rings, the stent being bent.

A second way to achieve micro structure in a stent involves the combination of one stent within another stent (slidably interfitted) in which the openings in the stents are mismatched or out of register relative to each other to provide an overall opening which is smaller than either of any of the two registered openings. That is, the openings do not exactly correspond with each other and are not exactly aligned with respect to each other. In such a situation each of the stents may have openings over a wide range of sizes which may or may not be individually micro porous but together in registration provide micro porous openings. However, when one stent is placed within the other and the openings are positioned out of alignment with respect to each other it can be seen that smaller openings through the combined stents can be achieved and can become micro porous even when the original openings are not. Such a structure is shown in FIGS. 2 and 3 in which an apertured stent 10a is being slidably interfitted with an apertured stent 10b. As can be seen in FIG. 3 when the two stents are completely combined, openings 12a in stent 10a when out of register with openings 12b in stent 10b will provide openings 12c of markedly smaller size than either of the openings 12a or 12b.

Such a combination may even include a third stent within the second stent and so forth. Each stent in such a case would be fabricated independently following which the stents would be slidably interfitted one into the other to provide the overall combination.

The combined stents if tightly fit together would not necessarily require any sort of fastening means. However, the stents may be joined as by welding or by the use of adhesives. If adhesives are used, the adhesives could be biodegradable or even contain a drug eluting material.

The primary purpose of using the second approach for achieving micro structure is based on the fact that it is easier to make fine holes through thin metal than through thick metal. Of course, for flexibility considerations, each interfitted stent will preferably be as thin as possible.

This concept of a stent within a stent has other ramifications as well. By fabricating each stent individually, one can achieve finer detail than if thicker material is used. A limiting factor in most fabrication processes is depth to width ratio. With a thin working layer the level of detail can be much finer.

Thus, even if one does not wish to fabricate a micro porous stent it may be advantageous to utilize the stent within a stent concept to provide stents which, although registered with each other in so far as the openings therein are concerned, would provide a combination having a finer level of detail in the opening configuration.

Thus, the concept of a stent within a stent, when viewed broadly, would not necessarily be limited to micro structure stents or to deformable stents but rather would be applicable broadly to stents in which it is desired to obtain finer detail in the configuration of the pattern making up the openings within the stent. This in addition to the primary purpose of the subject invention in which the combination of multiple layers, i.e., a stent within a stent to achieve stent strength and to create micro porous openings due to mismatch or lack of registration of the cell openings in each layer.

Presently, physicians sometimes implant a first stent and then implant a second stent within the first stent. An embodiment of this invention contemplates a further development of this practice by providing a stent within a stent combination already for implant. Thus the two stents may be implanted simultaneously. Several advantages are attendant with such a combination.

The prior practice of implanting first one stent followed by the implantation of a second stent within the first stent makes use of presently available stents of ordinary wall thickness. Such an implanted stent within a stent results in a relatively thick wall structure which is detrimental to flexibility and also to flow dynamics within the vessel.

By providing a combination stent within a stent prior to implantation, one may combine stents purposely made of less than ordinary wall thickness to achieve thinner overall stent structure which will exhibit improved overall performance such as:

Uniform vessel coverage
 less gapping
 small cell openings
improved flexibility
 layers can move relative to each other
customized strength provided by adding or subtracting layers of stent.

For example, referring now to FIG. 4, a schematic showing of a well known type of stent configuration, generally indicated at 20, made up of a series of serpentine annular rings 22 is shown. As can be seen in FIG. 4, when the stent is bent to accommodate vessel curvature, gaps 24 enlarge.

Figure 5:
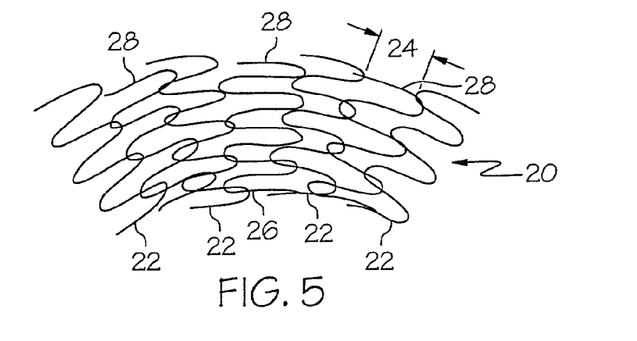
FIG. 5 is a schematic showing of a stent similar to that of FIG. 4 but including an inner stent arranged according to this invention.

Referring now to FIG. 5, a similar stent 20 is shown having the standard annular serpentine rings 22. However, included within the stent is a similar stent 26 arranged such that its rings 28 bridge the gaps 24 of the external stent 20 upon flexing or bending.

Figure 6:
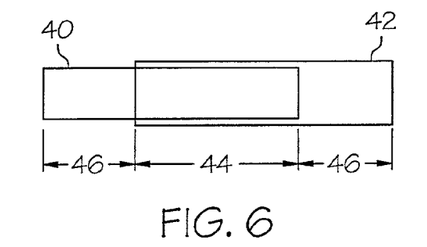
FIG. 6 is a schematic showing of a stent within a stent arranged according to this invention.

Customized stent strength may be accomplished by adding or subtracting stent layers. For example, refer to FIG. 6 which schematically shows a stent 40 partially within a stent 42. High strength is provided at region 44 where the two stents overlap and relatively low strength is provided at regions 46 where there is but a single stent structure. Such an arrangement provides a stent with soft ends.

Figure 7:
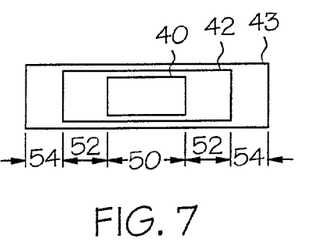
FIG. 7 is a schematic showing of three stents arranged within each other according to this invention.

Referring now to FIG. 7, a triple stent 40 within a stent 42 within a stent 43 is shown to provide three layers in region 50, two layers in regions 52 and a single layer in regions 54, thus providing three regions of different relative strength. Various other arrangements are available.

Figure 8:
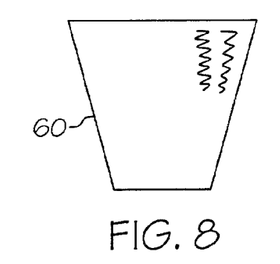
FIGS. 8-10 are schematic showings of another embodiment of the invention for providing multiple layer arrangements in a stent.
Figure 9:
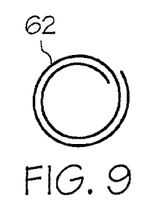
Figure 10:
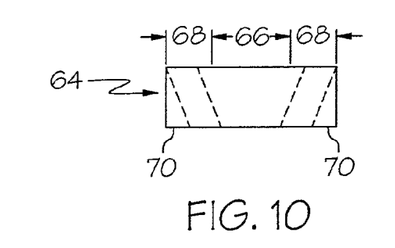

Lastly, variations in layers may be accomplished by rolling up a generally triangular shaped piece of metal sheet 60 shown in FIG. 8??? to form a cylinder 62 indicated in FIG. 9 which has in fact regions of various layers as shown in FIG. 10. In FIG. 10 it can be seen that, when rolled up, sheet 60 provides a cylindrical stent structure 64 having more layers in the mid regions 66 and successively fewer layers in regions 68 and even fewer in region 70.

The present invention is further directed to stents having variable thickness which exhibit improved radiopacity, MRI properties, flexibility and radial strength. In particular, the invention is further directed to expandable stents formed with a pattern adapted for radial expansion from a first unexpanded diameter to a second expanded diameter which approximates the inner diameter of the body lumen into which the stent is intended for implantation. The stents are further designed so as to have flexible portions which deform during bending and portions which provide improved radiopacity and radial strength which remain largely undeformed during bending.

When a stent is introduced into the vasculature of a patient, the stent must be flexible enough so that it can be navigated through the curves of the vasculature.

Also, in a typical stent, when it is expanded from its first unexpanded diameter to its second expanded diameter it will have portions which deform and portions which remain largely undeformed. A stent pattern may be designed in such a manner that the areas which flex coincide with the areas that deform during expansion.

The need for flexibility typically requires decreased stent thickness, while good radiopacity and radial strength require increased stent thickness. The present invention provides a stent having variable wall thickness which provides a balanced set of good properties, the relatively thicker sections providing for improved radial strength and radiopacity and the relatively thinner sections providing for good flexibility. The wall thicknesses of the stents of the present invention may range from about 0.002 to about 0.012" with wall thickness for thin walled construction being in the range of about 0.002" to about 0.004" and thicker walled construction being in the range of about 0.005" to about 0.010" although this may vary. The outside diameter of the tubing may range from about 0.060" to about 0.16" (about 1.5 mm to about 4 mm) and more suitably in the range of about 0.060" to about 0.075" (1.5 mm to about 2 mm).

The tubular members, which may also be referred to as stent performs or stent blanks, may be manufactured from any materials known in the art for use in forming such members, and suitably the tubular members may be made of a biocompatible material. Examples include, but are not limited to, the shape memory materials, noble metals, transition metals, any alloys of the shape memory materials, noble metals, transition metals, polymeric materials, and so forth.

The shape memory materials useful herein include, but are not limited to, binary shape-memory metals such as NITINOL® which is a nickel-titanium alloy, or other alloys of nickel and titanium and doped binary metals such as chromium, niobium, vanadium, and so forth. Additional suitable shape-memory alloys are disclosed in WO 95/31945, the contents of which are incorporated by reference herein in their entirety.

Examples of useful stainless steel alloys include, but are not limited to, Special Chemistry of type 316L SS per ASTM F138-92 or ASTM F139-92 grade 2, and so forth.

Other metals suitable for formation of the inventive stents of the present invention include, but are not limited to the more radiopaque metals including the noble metals gold and platinum, and tantalum; iridium, palladium, tungsten, titanium, chromium, cobalt, molybdenum, nickel, niobium, palladium, iridium, vanadium, barium, hafnium, silver, copper, zinc, aluminum, and so forth, and alloys thereof.

Employing materials such as platinum, tantalum, niobium, titanium, and alloys thereof, may be beneficial because they are highly compatible with and safe for use with MRI.

Specific examples of alloys useful for manufacture of the inventive stents herein include, but are not limited to, nickel-titanium, cobalt-chromium, cobalt-chromium-molybdenum, titanium-chromium, titanium-aluminum-vanadium (Ti6Al4V), and so forth.

The above materials are known to those of skill in the art and those listed are intended for exemplary purposes only. This list is by no means exhaustive of the types of materials which may be employed in the manufacture of the stents of the present invention.

Figure 11A:
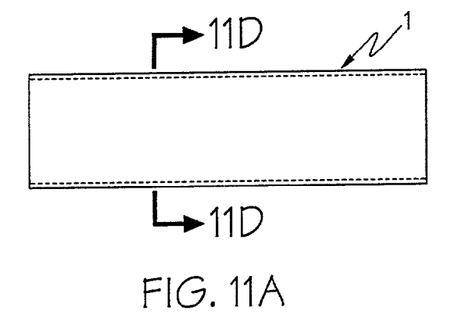
FIG. 11a is a side view of a tubular member having no cut-out regions.
Figure 11B:
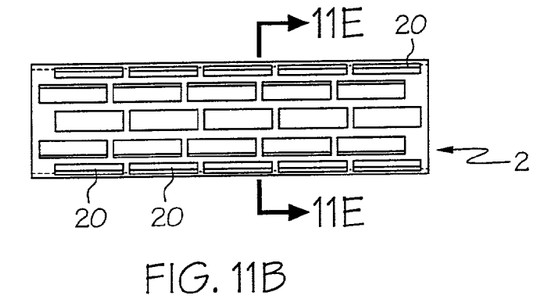
FIG. 11b is a side view of a tubular member having cut-out regions.
Figure 11C:
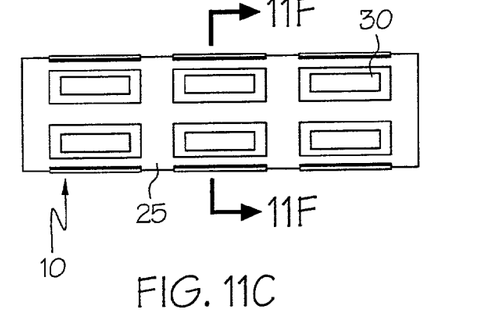
FIG. 11c is a side view of the inventive stent of the present invention after joining the tubular member shown in FIG. 11a with the tubular member shown in FIG. 11b.

In one embodiment, the present invention is directed to a stent manufactured of at least a first and second tubular member. The first tubular member includes cut-out regions, and the second tubular member may or may not have cut-out regions. The tubular members are suitably of a thin-walled construction. FIG. 11a illustrates generally at 1, a tubular member of a thin-walled construction and having no cut-out regions. FIG. 11b illustrates generally at 2, a tubular member having cut-out regions 20. Tubular member 2 may also be of a thin-walled construction. FIG. 11c illustrates generally at 10, a stent made by placing tubular member 2 over tubular member 1 as shown.

The term cut-out as used herein is not intended to refer to any particular method of producing such regions in the tubular member and thus contemplates any methods known in the art including, for example, laser and chemical etching, and so forth.

In this particular embodiment, tubular member 2 having the cut-out regions 20 is slightly larger than tubular member 1 and is fitted over tubular member 1 forming stent 10 which has variable thickness. The cut-out regions 20 of tubular member 2 may be created by any methods known to those of skill in the art including laser machining or machine or chemical etching, for example.

The tubular members may be interference fit or line-to-line fit, for example, or they may be fitted together so that a slight gap exists between the tubular members which is subsequently closed during balloon expansion, for example. The tubular members may be secured together using any method known in the art including, but not limited to, welding, friction welding, brazing, diffusion bonding, co-drawing or co-rolling as sheet metal to create a metallurgical bond, and so forth.

Figure 11D:
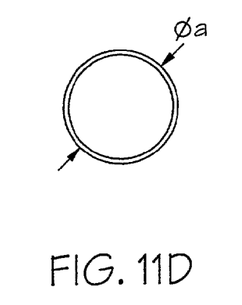
Figure 11E:
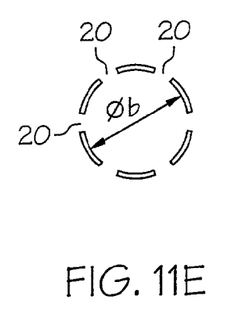
FIG. 11e is a cross-sectional view of the same tubular structure shown in FIG. 11b.
Figure 11F:
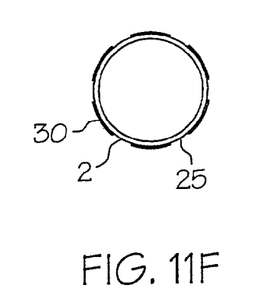
FIG. 11f is a cross-sectional view of the stent shown in FIG. 11c.

Some areas of stent 10 have only one layer where the cut-out regions 20 exist on tubular member 2 and some have a double layer where there are no cut-out regions. A cross-sectional view of a section of tubular member 1 is shown at A-A in FIG. 11d and a cross-sectional view of a section of tubular member 2 is shown at B-B in FIG. 11e. A cross-sectional view of a section of stent 10 is shown at C-C in FIG. 11f. This embodiment offers a stent having improved flexibility in the areas of the stent having only a single layer shown by reference numeral 25, i.e. where the cut-out regions 20 of tubular member 2 overlap tubular member 1. Thin walled materials allows for reasonable balloon expansion pressures.

The sections of the stent having a double layer shown by the reference numeral 30 exhibit improved radiopacity and also improve the radial stiffness and resistance to radial compression. The result of having at least two layers for the x-rays to pass through results in more contrast on the x-ray film or fluoroscopy screen which results in enhanced radiopacity. Furthermore, reducing the ferromagnetic strength of a monolithic stent such as a 316L stainless steel stent by employing a stent having one layer which is 316L stainless steel and one which is formed of a highly MRI safe and compatible material such as titanium, platinum, tantalum or niobium, for example, may result in improved MRI safety and compatibility.

Figure 12A:
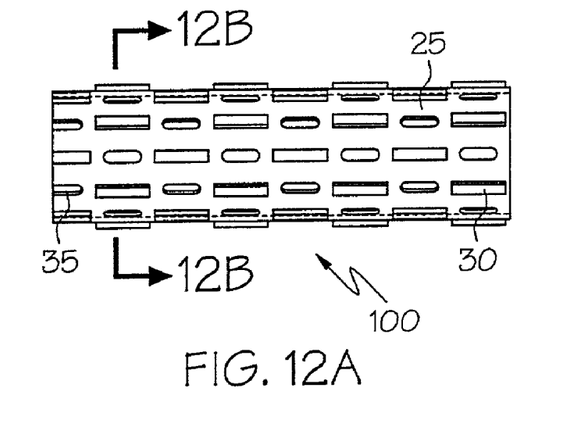
FIG. 12a is a side view of an alternative embodiment of the inventive stent of the present invention.
Figure 12B:
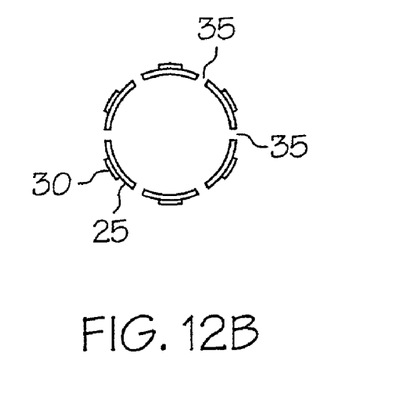

FIG. 12a illustrates generally at 100, an alternative embodiment of the inventive stent of the present invention in which stent 100 has not only areas which have a single layer thickness 25 and areas which have a double layer thickness 30, but also has areas which are cut-out through both layers represented by reference numeral 35. In this embodiment, both tubular members have cut-out regions 20 which substantially align with one another therefore creating sections in the finished stent 100 which are cut-out through both layers. The cut-out regions may be created in each tube prior to assembly, or the cut-out regions may be created in tubular member 2 by laser machining or chemical or laser etching, for example after tubular member 1 has been fitted over tubular member 2. In the latter case, tubular member 2, being slightly larger than tubular member 1, is first fitted over tubular member 1 and the cut-out regions in tubular member 1 may be created by laser or chemical etching the cut-out regions in 1 which will therefore substantially match those cut-out regions 20 of tubular member 2. However, tubular member 1 may have fewer cut-out regions than tubular member 2 as desired. A cross-sectional view of this embodiment of the inventive stent of the present invention is taken at section A-A and shown in FIG. 12b.

In one embodiment of the present invention, both tubular member 1 and tubular member 2 are manufactured of the same material. In this embodiment, the material employed may be stainless steel 316L, stainless steel 304L, nickel-titanium alloy such as NITINOL®, CoCrMo alloy, titanium alloy, tantalum or its alloys, platinum or its alloys, for example. Alternatively, the material may be polymeric.

Employing the same material for making both tubular members increases manufacturing efficiency because the design, formation, laser machining, cleaning, and passivation of the tubular members can be done more expeditiously with one material than if dissimilar materials are employed.

In an alternative embodiment, the thickness and/or other properties of the stent may be further varied over its surface by varying the thickness and/or properties of tubular member 1 using methods known in the art such as, for example, annealing or other heat treating techniques, or by machining techniques, and so forth which will produce a wall in the tubular member having thinner and thicker regions and/or other variable properties. The thickness and/or other properties of tubular member 2 may also be varied.

Alternatively, more than two tubes may be employed in the present invention as well to create more than two layers in the finished composite stent structure. For example, 3, 4, 5 or more tubular members may be employed to produce composite stents having 3, 4, 5 or more layers.

Figure 13A:
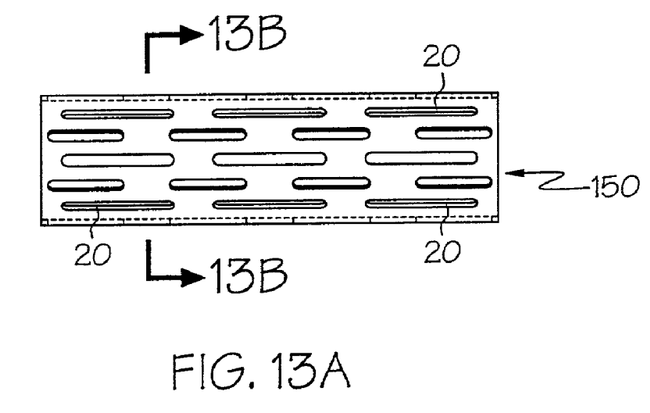
FIG. 13a is a side view of a prior art stent formed of a single tubular member.
Figure 13B:
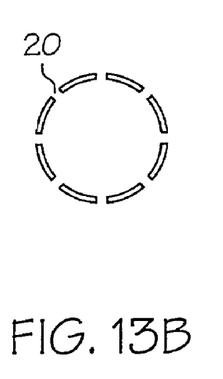

In contrast, FIG. 13a illustrates generally at 150, a prior art stent formed of a single tubular member. FIG. 13b is a cross-sectional view of the prior art stent shown in FIG. 13a.

Configuration of a specific stent design may also be employed to create improved radiographic contrast on the fluoroscopy screen, as well as improved radial strength and improved flexibility. For example, FIG. 14 illustrates several different stent configurations. Such configurations may be formed using methods known to those in the art including, but not limited to, tube drawing, extruding through a shaped die or by honeycomb construction techniques, for example.

Figure 14A:
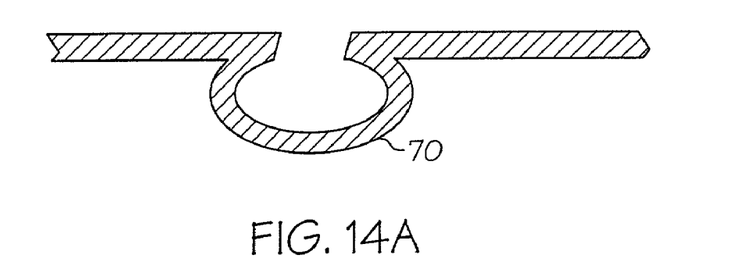
FIGS. 14a-c illustrate several different inventive stent patterns.
Figure 14B:
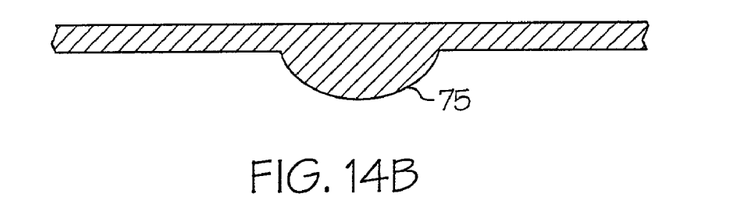
Figure 14C:
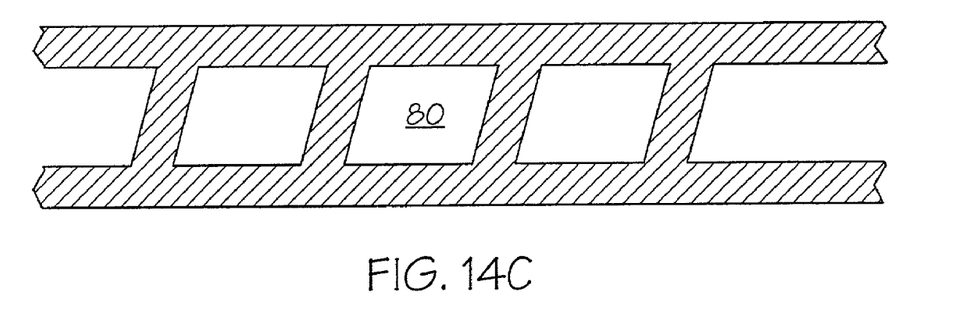
Figure 14D:
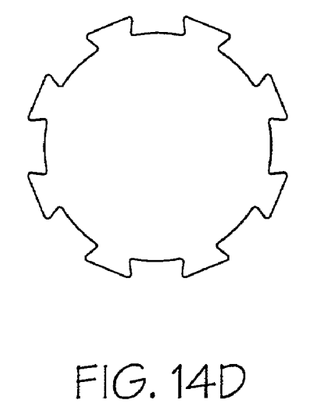

FIGS. 14a-14c illustrates several different stent patterns designed to create regions of the stent that will produce more radiographic contrast on a fluoroscopy screen and more radial strength, as well as having regions of increased flexibility. FIG. 14a is a side view of a portion of a stent having a pattern which includes an oval protrusion 70. This protrusion includes a void in the center of the protrusion in contrast to the pattern shown in FIG. 14b. The present invention also contemplates other similar patterns which have more distinct corners as well. FIG. 14d is an end view of the stent employing the pattern described in FIG. 14a.

Figure 14E:
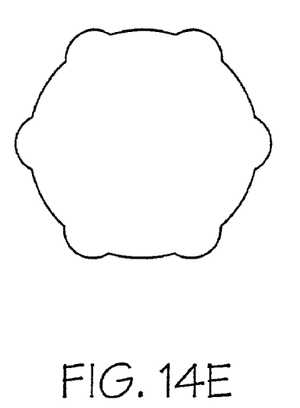
FIG. 14e shows an end view of the same stent pattern as shown in FIG. 14b.

FIG. 14b is a side view of a portion of a stent having a pattern which includes a solid protuberance, i.e. is formed in the stent material and does not have a void in its center. This pattern may be varied as well by changing the geometry without departing from the scope of the present invention. FIG. 14e is an end view of the stent employing the pattern described in FIG. 14b.

Figure 14F:
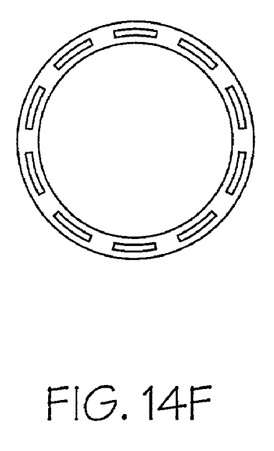
FIG. 14f shows an end view of the same stent pattern as shown in FIG. 14c in an unexpanded state.
Figure 14G:
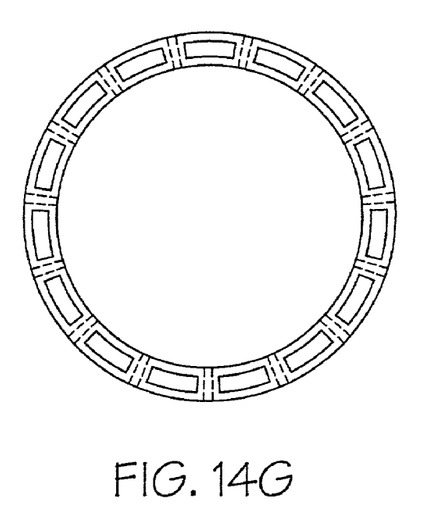
FIG. 14g shows an end view of the same stent pattern as shown in FIG. 14c in an expanded state.

FIG. 14c is a side view of a portion of a stent employing a honeycomb pattern which also may be employed to increase the radiographic contrast of the stent while maintaining the radial strength and flexibility. FIG. 14f is an end view of a stent employing the pattern described in FIG. 14c in an unexpanded state while FIG. 14g is an end view of the same stent as in FIG. 14f shown in an expanded state.

The above described patterns create areas of greater radiographic contrast thus making the stent more visible using fluoroscopic techniques. These patterns may be employed in the multi-tubular stent structure as described above, and may be employed in creating a stent of a single tubular member as well.

Figure 15:
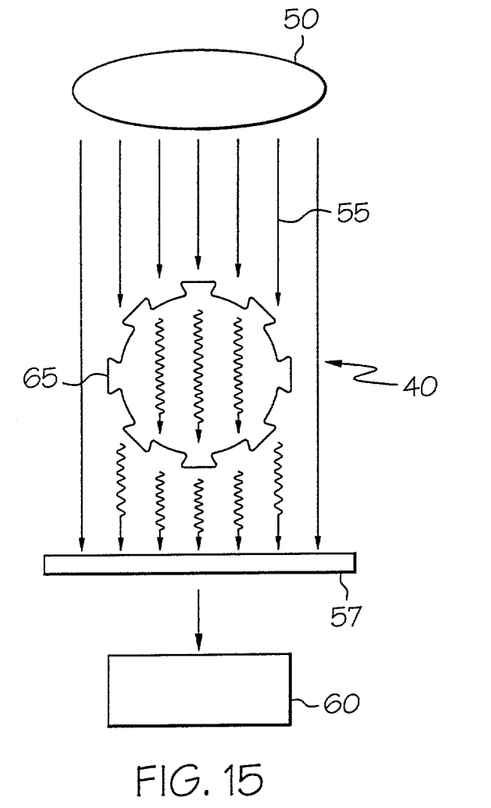
FIG. 15 shows a cross-section of an inventive stent pattern of the present invention subjected to x-rays.

FIG. 15 illustrates generally at 40, an end view of an inventive stent of the present invention employing a pattern similar to that shown in FIG. 14a. The stent has an oval protuberance 65 creating more complexity in the stent pattern and thus creating regions of more radiographic contrast on the fluoroscopy screen 60 when the stent is subjected to a source of x-rays 50. The oval protuberances 65 act as x-ray absorbers, thus the creation of more radiographic contrast and visibility on the fluoroscopy screen 60.

Figure 16:
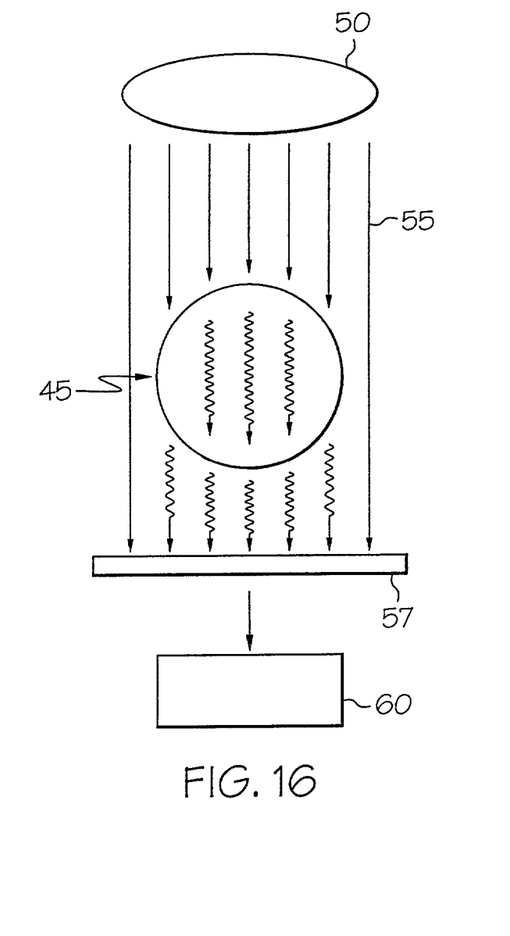
FIG. 16 shows a cross-section of a prior art stent subjected to x-rays.

In contrast, in the case of a conventional stent which is shown in an end view generally at 45 in FIG. 16, where there are no areas to absorb more of the x-rays 50, less radiographic contrast will be exhibited by the stent 45 when viewed on the fluoroscopy screen 60.

Employing the stent patterns as described above results in a stent which has areas which are thicker, or which are more complex, providing more radiographic contrast on a fluoroscopy screen and more radial strength, and areas which are thinner resulting in more flexibility.

Simply increasing the thickness of a stent material to improve radiopacity, in contrast, can result in higher balloon pressures required to expand the stent which in turn can result in more injury of the vessel, and more restenosis ultimately, as well as decreased maneuverability through the vasculature, while simply decreasing the wall thickness of a stent results in improved flexibility but decreased visibility using fluoroscopic techniques. FIG. 16 shows a cross-section of a typical stent design.

In another embodiment of the present invention, the radiographic contrast, radial strength and the flexibility of the stent are improved by employing a tubular perform having a plurality of first and second sections each having a first end and a second end. The first sections are formed of a first material and the second sections are formed of a second material which is more radiopaque than the first material. The first material may be an alloy or a blend of materials and the second section may be an alloy or blend of materials which results in a blend which is more radiopaque that the first material. The first sections are joined to the second sections end to end in a butt joint fashion. The materials are also selected such that some sections are more flexible, and some sections are radially stronger and have better radiopacity. The thickness of a section may also be varied in order to achieve the desired balance, and some sections may be thicker than other sections as well.

Figure 17:
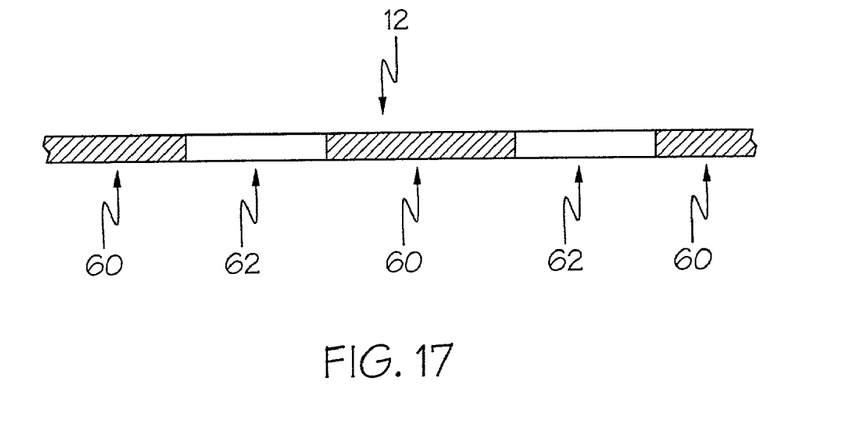
FIG. 17 illustrates an embodiment in which the tubular stent perform is formed of tubular sections of different materials joined end to end.

FIG. 17 illustrates generally at 12 a tubular preform of this type in which a first section 60 formed of a first material is joined end to end with a second section 62 formed of a second material which is more radiopaque than the first material. The first material may be a flexible material such as stainless steel or a shape memory alloy such as NITINOL®, while the second material may be formed of a more rigid, radiopaque material such as gold, tantalum, platinum, and so forth, or alloys thereof.

The sections of tubing may be joined using any methods known in the art including, but not limited to, welding including laser welding, brazing, rolling, bonding, drawing, and so forth. However, no mechanical securement other than contact is required, particularly for tubing which is employed in a mechanically expandable stent such as those expanded using an inflation member, for example, a dilatation balloon.

Once formation of the tubular preform or stent blank is complete, the stent pattern may be cut into the preform using methods known to those of skill in the art including laser and chemical etching, for example.

Yet another alternative embodiment for forming stents having variable thickness for achieving optimum properties involves the use of a polygonal shaped stent preform. The polygonal shape may be any geometric shape which has 3 or more sides including a triangle, pentagon, hexagon, octagon, and so forth. Suitable, hexagons or octagons are employed in the present invention and most suitably, an octagon is employed. The polygonal shape may be formed during extrusion or by machining, for instance. Material from the inner surface of the preform may be removed using any methods known in the art including, but not limited to, machine grinding, lasering, etching, and so forth.

Figure 18A:
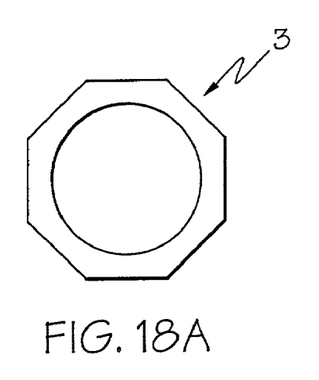
FIG. 18a-18c illustrate several different polygonal stent performs prior to cutting the stent pattern.
Figure 18B:
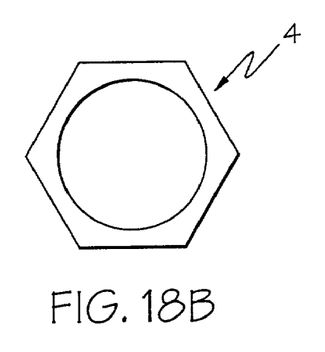
Figure 18C:
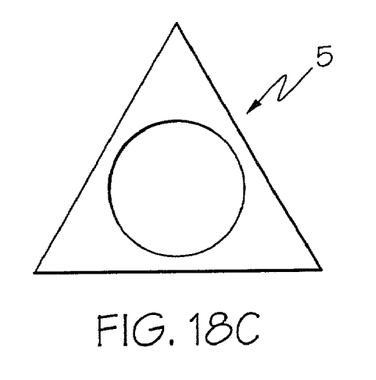

One method involves the placement of the tubing, i.e. the preform or blank, in a rotatable collet fixture of a machine-controlled apparatus for positioning the tubing relative to a laser. The tubing is then rotated relative to the laser which is also machine-controlled. The laser then evenly removes material from the tubing by ablation. This automatically results in a stent preform having variable thickness around the circumference due to the shape of the preform. FIGS. 18a-18c represent several different polygonal performs after removal of material from the inner surface of the preform. FIG. 18a illustrates generally at 3 a octagonal preform; FIG. 18b represents generally at 4 a hexagonal preform; and FIG. 18c represents generally 5 a triangular preform. It is apparent from the figures that the result is a variable thickness stent.

Once the desired amount of material has been removed, the stent pattern may then be cut into the preform using methods known in the art such as laser and chemical etching. The stent pattern is designed to match with the thicker and thinner portions of the stent preform in order to optimize the flexibility and radiopacity.

The above disclosure is intended to be illustrative and not exhaustive. The description will suggest many variations and alternatives to those of ordinary skill in the art. All of these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A method of making a stent having variable thickness, the stent having a pre-delivery state and a post-delivery state, the method comprising the steps of:
   providing a first tubular member having cut-out regions;
   providing a second tubular member; and
   assembling said first tubular member over said second tubular member or said second tubular member over said first tubular member to form a layered stent perform wherein a significant portion of said first tubular member overlaps said second tubular member; and
   fixing said first and said second tubular members together by machining, brazing, co-rolling or co-drawing, said first tubular member and said second tubular member fixed together during both the pre-delivery state and the post-delivery state.

2. The method of claim 1 wherein said assembling and said fixing steps are simultaneous.

3. The method of claim 1 wherein said first tubular member is fitted over said second tubular member.

4. The method of claim 1 further comprising a step of cutting a desired pattern in said layered tubular preform.

5. The method of claim 1 wherein said first tubular member and said second tubular member are formed of the same material.

6. The method of claim 1 wherein said first tubular member is formed of a different material than said second tubular member.

7. The method of claim 1 wherein said first tubular member and said second tubular member are formed from shape memory materials, noble metals, transition metals, alloys thereof, polymers, and mixtures thereof.

8. The method of claim 1 wherein said first tubular member and said second tubular member are formed from nitinol, stainless steel, titanium, tantalum, platinum, gold, cobalt, chromium, molybdenum, niobium, any alloys thereof, and mixtures thereof.

9. The method of claim 1 wherein the thickness of said first tubular member or said second tubular member is varied over the surface.

10. The method of claim 1 wherein said second tubular member has cut-out regions which align with the cut-out regions of said first tubular member.

11. The method of claim 1 wherein at least about one third of said first tubular member is assembled over said second tubular member or at least about one third of said second tubular member is assembled over said first tubular member to form a layered stent perform.

12. The method of claim 1 wherein at least about one half of said first tubular member is assembled over said second tubular member or at least about one half of said second tubular member is assembled over said first tubular member to form a layered stent perform.

13. The method of claim 1 wherein the entirety of said first tubular member is assembled over said second tubular member or the entirety of said second tubular member is assembled over said first tubular member to form a layered stent perform.

14. A method of making a stent having variable thickness comprising the steps of:
   providing a first tubular member having cut-out regions which define cells;
   providing a second tubular member having cut-out regions which define cells; and
   assembling said first tubular member over said second tubular member or said second tubular member over said first tubular member to form a layered stent preform such that the cells of said first tubular member overlap with and are mismatched with the cells of said second tubular member.

15. A method of making a stent having variable thickness, the stent having a pre-delivery state and a post-delivery state, the method comprising the steps of:
   providing a first tubular member having cut-out regions;
   providing a second tubular member having a thin-walled construction; and
   assembling said first tubular member over said second tubular member or said second tubular member over said first tubular member to form a layered stent perform wherein a significant portion of said first tubular member overlaps said second tubular member, said first tubular member and said second tubular member assembled during said pre-deliveiy state and said post-delivery state,
   wherein said first tubular member is formed from a different material than said second tubular member.

16. The method of claim 15 wherein the second tubular member has cut-out regions, at least some of the cut-out regions of the first tubular member overlapping some of the cut-out regions of the second tubular member.

17. The method of claim 15 wherein at least some of the cut-out regions of the first tubular member overlapping some of the cut-out regions of the second tubular member.

18. A method of making a stent having variable thickness comprising the steps of:
   providing a first tubular member having cut-out regions which define cells;
   providing a second tubular member; and
   assembling said first tubular member over said second tubular member or said second tubular member over said first tubular member to form a layered stent perform wherein multiple regions of said second tubular member are overlapped by said first tubular member or wherein multiple regions of said first tubular member are overlapped by said second tubular member, and
   fixing said first and said second tubular members together by brazing, co-rolling or co-drawing.

19. A method of making a scent having variable thickness comprising the steps of:
   providing a first tubular member having cut-out regions;
   providing a second tubular member; and
   assembling said first tubular member over said second tubular member or said second tubular member ova said first tubular member to form a layered stent perform;
   wherein the first tubular member and the second tubular member are secured by mechanical contact only.

* * * * *